United States Patent
Zigler et al.

(10) Patent No.: US 7,718,436 B2
(45) Date of Patent: May 18, 2010

(54) METHOD FOR MULTI-BATCH PRODUCTION OF FDG

(75) Inventors: Steven S. Zigler, Knoxville, TN (US); Joseph C. Matteo, Knoxville, TN (US); Thomas Mangner, Chelsea, MI (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1442 days.

(21) Appl. No.: 10/421,324

(22) Filed: Apr. 23, 2003

(65) Prior Publication Data

US 2004/0022696 A1   Feb. 5, 2004

Related U.S. Application Data

(60) Division of application No. 09/795,744, filed on Feb. 28, 2001, now abandoned, which is a continuation-in-part of application No. 09/569,780, filed on May 12, 2000, now Pat. No. 6,599,484.

(51) Int. Cl.
*G01N 23/00* (2006.01)

(52) U.S. Cl. .................. 436/57; 436/179; 436/180; 422/99; 422/101; 422/102; 376/194; 376/195

(58) Field of Classification Search ............ 422/68.1, 422/99, 102, 104, 101; 376/194–202; 436/57, 436/174, 180, 504, 545; 424/1.89
See application file for complete search history.

(56) References Cited

U.S. PATENT DOCUMENTS

| | | | |
|---|---|---|---|
| 4,736,638 A | | 4/1988 | Okawa et al. |
| 4,794,178 A | | 12/1988 | Coenen et al. |
| 4,872,974 A | * | 10/1989 | Hirayama et al. ............ 210/90 |
| 5,012,845 A | | 5/1991 | Averette |
| 5,037,602 A | * | 8/1991 | Dabiri et al. ................ 376/198 |
| 5,064,529 A | | 11/1991 | Hirayama et al. |
| 5,169,942 A | | 12/1992 | Johnson et al. |
| 5,280,505 A | * | 1/1994 | Hughey et al. .............. 376/156 |
| 5,282,380 A | * | 2/1994 | DiLeo et al. .................. 73/38 |
| 5,417,101 A | * | 5/1995 | Weich .......................... 73/38 |
| 5,468,355 A | * | 11/1995 | Shefer et al. ............. 204/157.2 |
| 5,554,811 A | | 9/1996 | Rokugawa et al. |
| 5,573,747 A | * | 11/1996 | Lacy ........................ 424/1.65 |
| 5,594,161 A | * | 1/1997 | Randhahn et al. ............. 73/38 |
| 5,855,851 A | | 1/1999 | Matsubara et al. |

(Continued)

OTHER PUBLICATIONS

Link, Jeanne M.; Clark, John C.; Ruth, Thomas J., Introduction: State of the Art in Automated Syntheses of Short-Lived Radiopharmaceuticals, Targetry '91, 1991.

*Primary Examiner*—Jill Warden
*Assistant Examiner*—Dwayne K Handy
(74) *Attorney, Agent, or Firm*—Peter Kendall

(57) ABSTRACT

A method of producing multiple batches of a radiopharmaceutical, such as FDG. The method includes the steps of transferring the appropriate liquids to a production apparatus, processing the liquids to produce the radiopharmaceutical, delivering the radiopharmaceutical to a container, automatically cleaning the apparatus, and repeating the previous steps, as desired. The apparatus for multi-batch production of FDG includes a reagent delivery system, a reaction vessel, a filter assembly, and a control system. The combination of these components provides a method that is capable of producing multiple batches of a radiopharmaceutical with minimal operator intervention and, consequently, minimal radiation exposure.

14 Claims, 7 Drawing Sheets

U.S. PATENT DOCUMENTS

| | | | |
|---|---|---|---|
| 5,932,178 A * | 8/1999 | Yamazaki et al. | 422/159 |
| 6,011,825 A * | 1/2000 | Welch et al. | 376/195 |
| 6,143,573 A | 11/2000 | Rao et al. | |
| 6,172,207 B1 * | 1/2001 | Damhaut et al. | 536/18.4 |
| 6,190,617 B1 | 2/2001 | Clark et al. | |
| 6,241,947 B1 | 6/2001 | Komatsu et al. | |
| 6,372,183 B1 | 4/2002 | Akong et al. | |
| 6,567,492 B2 * | 5/2003 | Kiselev et al. | 376/195 |
| 6,845,137 B2 * | 1/2005 | Ruth et al. | 376/195 |

* cited by examiner

METHOD FOR MULTI-BATCH PRODUCTION OF FDG

CROSS-REFERENCE TO RELATED APPLICATIONS

This Application is a Divisional of U.S. application Ser. No. 09/795,744, filed Feb. 28, 2001, now abandoned, which is a Continuation-In-Part of U.S. application Ser. No. 09/569,780, filed on May 12, 2000, now U.S. Pat. No. 6,599,484.

STATEMENT REGARDING FEDERALLY SPONSORED RESEARCH OR DEVELOPMENT

Not Applicable

BACKGROUND OF THE INVENTION

1. Field of Invention

This invention relates to a reagent delivery system for use in the production of radiopharmaceuticals for positron emission tomography (PET). More specifically, it relates to a method of multi-batch production of $^{18}$F-labeled glucose, known as fluorodeoxyglucose or "FDG."

2. Description of the Related Art

Positron Emission Tomography is a powerful tool for diagnosing and treatment planning of many diseases wherein radiopharmaceuticals or radionuclides are injected into a patient to diagnose and assess the disease. For example, the radiopharmaceutical $^{18}$F-labeled glucose, known as fluorodeoxyglucose or "FDG", can be used to determine where normal glucose would be used in the brain. FDG is a labeled compound in which a fluorine-18 ion ($^{18}$F) is substituted for part of the glucose. FDG labeled in this manner is a desirable radiopharmaceutical because the fluorine-18 is a positron emission nuclide with a half-life period of 109.7 minutes.

The production of PET radiopharmaceuticals requires the use of various reagents and solutions to effect the necessary chemical conversions. The reagents and solutions must be delivered to a reaction vessel, where the conversions take place. The deliveries must be accurate, reproducible and, in addition, there must be minimal cross-contamination between the various reagents. A more detailed discussion of this type of delivery system is disclosed in the above-referenced patent application Ser. No. 09/569,780, filed on May 12, 2000.

Generally, the production of FDG includes the steps of bombarding a target material with a particle beam, mixing the target material with other materials, processing the resulting compound in a reaction vessel, and filtering the product. An accelerator produces radioisotopes by accelerating a particle beam and bombarding a target material, housed in a target system, with the particle beam. To produce FDG, the product of bombardment, fluorine-18 ions, is further processed to produce a substance suitable for injection into the human body. These ions are further processed to produce FDG (2-deoxy-2-fluoro-D-glucose) in a process typically referred to as radiosynthesis.

Well known in the art are various methods for producing FDG. For example, U.S. Pat. No. 4,794,178 issued to Coenen at al. on Dec. 27, 1988 discloses a process for labeling organic compounds with fluorine-18 through a nucleophilic substitution reaction. U.S. Pat. No. 5,169,942 issued to Johnson at al. on Dec. 8, 1992 discloses a method for making FDG that uses a phase-transfer reagent U.S. Pat. No. 5,932,178 issued to Yamazaki at al. on Aug. 3, 1999 discloses an FDG synthesizer that uses a labeling reaction resin column. Although these patents disclose various methods of FDG production, none of these patents teach a method that addresses the specific objects and advantages of the present invention.

Fluorine-18 is a radioactive material to which human exposure should be limited. Also, the particle beam striking the target material is a radioactive process, which should also have limited human exposure. Accordingly, the radiation exposure to persons producing the FDG is an important consideration. Toward this end, efforts have been made to automate the production of radioisotopes, in particular, FDG.

Automation of radionuclide and radiochemical syntheses is discussed in a paper entitled "Introduction: State of the Art in Automated Syntheses of Short-lived Radiopharmaceuticals" by Jeanne M. Link, John C. Clark, and Thomas J. Ruth, Targetry '91, pp 174-185. At page 174, the paper discusses the advantages and disadvantages of the various levels of automation, including manual and remote operation, remote automated operation, and robotic operation. Specifically, the paper identifies the advantages of automation as a reduction of radiation exposure and a reduction of time to perform radiosynthesis. Furthermore, at page 183, the paper describes self-cleaning automated FDG systems.

Many commercially available components can be used to automate the production of FDG. Valves, tubing, and fittings are well known in the art and are well suited to this application. So too are membrane filters. Other components are specially designed for the process. See, for example, the reaction vessel disclosed in the above-referenced patent application Ser. No. 09/569,780, filed on May 12, 2000, and the related patent application Ser. No. 09/795,744 filed on Feb. 28, 2001 by Zigler, et al.

Although the prior art systems have proven successful for the production of FDG, there exists a need for further automation, including the capability of producing multiple batches of FDG with minimum operator intervention. Furthermore, to minimize operator intervention, multi-batch capability requires that the apparatus be self-cleaning and include automated testing of components, such as the membrane filters.

Therefore, it is an object of the present invention to provide an apparatus for performing multiple FDG production runs with a single set up.

It is another object of the present invention is to minimize radiation exposure to the apparatus operators.

It is yet another object of the present invention to provide an apparatus that is easy to handle and economic to use.

Another object of the present invention is to provide an apparatus that is self-cleaning.

Still another object of the present invention is to provide an apparatus which includes means for automating the pressure integrity test of the membrane filtration device used in final product sterilization.

BRIEF SUMMARY OF THE INVENTION

According to a preferred embodiment of the present invention, a method for multi-batch production of FDG is disclosed. The method includes the steps of selecting the reagents necessary for producing FDG, transferring said reagents to a reaction chamber, producing FDG, filtering the produced FDG, delivering the FDG to a container, cleaning the production apparatus, and repeating the previous steps to produce multiple batches of FDG.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
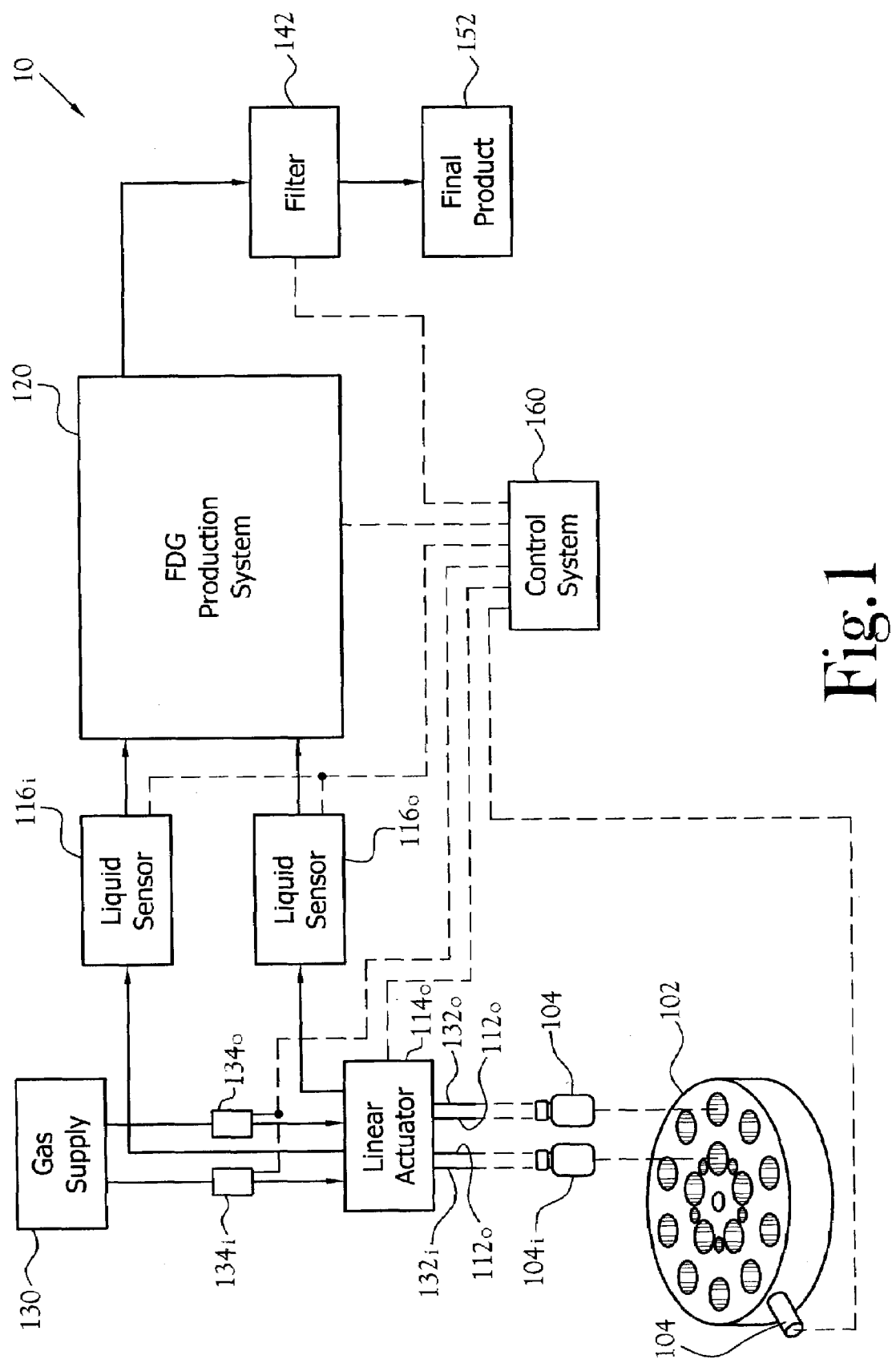
FIG. 1 is a block diagram of an apparatus for multi-batch production of FDG.

FIG. 1 illustrates a preferred embodiment of the present invention which comprises a reagent delivery system 10 for an automated apparatus for multi-batch production of FDG. The reagent delivery system 10 includes a rotary carousel 102, a linear actuator 114 with needles 112, 132 used for liquid transfer, a plurality of liquid sensors 116, an FDG production system 120, a filter assembly 142, and a control system 160. The reagent delivery system 10 uses electronic mass flow controllers 134 and various valves, tubing, and fittings.

Figure 2:
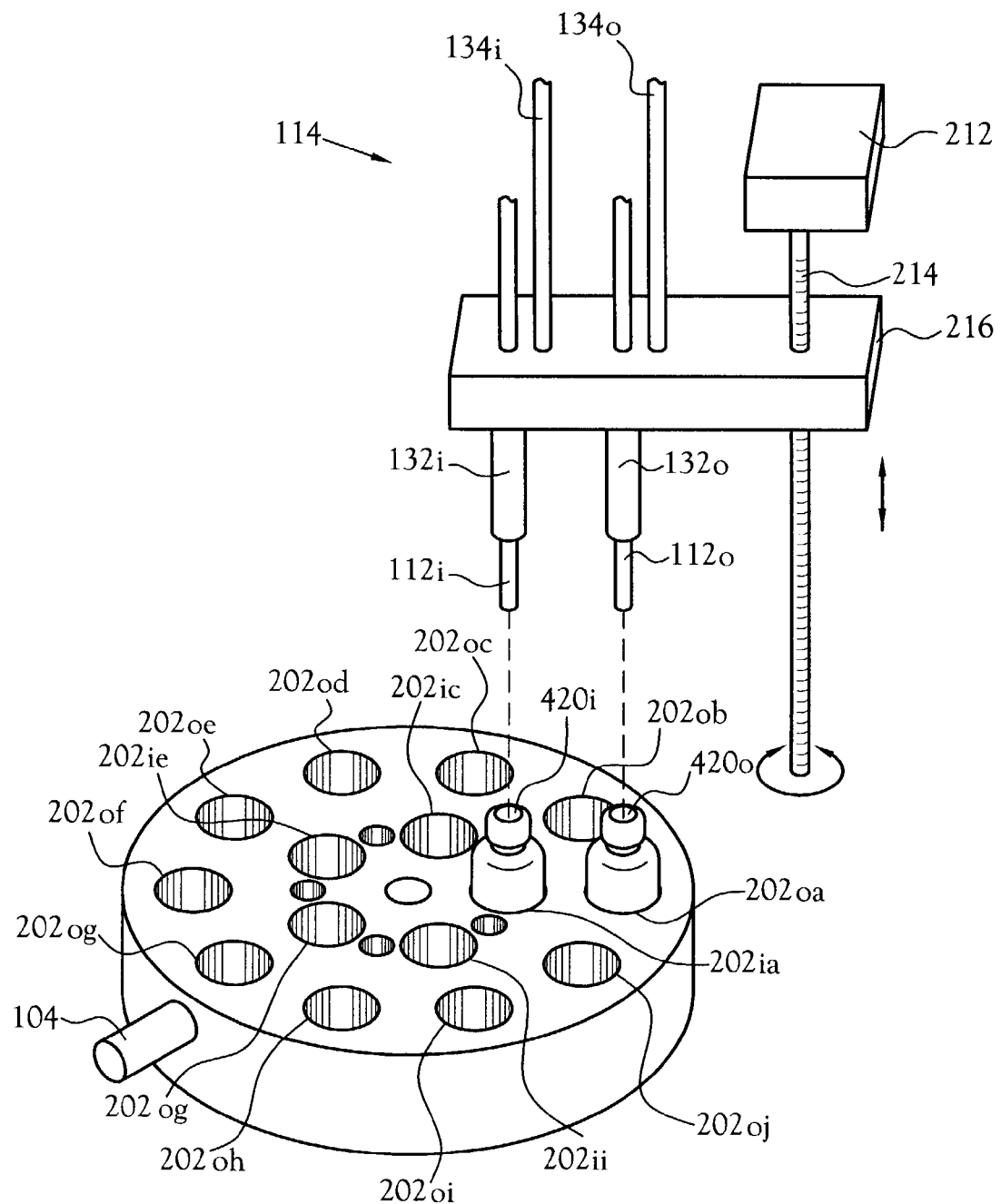
FIG. 2 is a pictorial view of the reagent carousel and linear actuator with two concentric needles.

FIGS. 1 and 2 show the rotary carousel 102, which holds a plurality of septum-sealed glass vials 104 containing the reagents and solvents used in the production process. A variety of reagents and solutions are necessary for the production of FDG. In addition, solvents are necessary for cleaning the apparatus between production runs. Vials 104 containing the necessary quantities of these reagents and solvents are placed in the rotary carousel 102. The use of the rotating carousel 102 permits a single group of needles 112, 132 to be used to transfer these reagents and solvents. The rotary carousel 102 rotates on a pneumatically driven mechanism 106 that has positional feedback for the control system 160. A spring loaded detent mechanism assures accurate positioning of the rotary carousel 102. The control system 160 causes the pneumatical drive mechanism 106 to rotate the rotary carousel 102 so that the desired vials 104 are positioned under the needles 112, 132 used to transfer the liquid. Finally, the rotary carousel 102 is readily removable to allow access to the vials 104. Those skilled in the art will recognize that an in-line vial holder having a linear transfer mechanism can be used without interfering with the objects and advantages of the present invention.

In the preferred embodiment, the rotary carousel 102 has two concentric rings of holes 202 in which the vials 104 are placed. Five vials 104i fit in the inside ring of holes 202i, and ten vials 104o fit in the outside ring of holes 202o. Vials with tight internal diameter tolerances are commercially available, such as those by Kimble Glass Inc. The vials 104 may be large volume (20 ml) or small volume (10 ml), and are securely mounted in the individual vial holes 202. Also in the inside ring are smaller holes or slots placed between the openings for the vials 104i. The purpose of these smaller holes or slots is to provide a place for the inside needles 112i, 132i to pass when the rotary carousel 102 is positioned so that only one outside vial 104 is being used. The reagent which is the target material is placed in the inside vials 104i.

As illustrated in FIG. 2, the linear actuator 114 positions the needles 112, 132 vertically above either one or two vials 104 in the rotary carousel 102. Separate sets of needles 112, 132 are used to access the vials 104 in the inner and outer rings of the rotary carousel 102. Referring to FIG. 2, the linear actuator 114 includes a set of needles 112, 132 mounted on a head 216, which mounts to a screw shaft 214. When an electric motor 212 turns the shaft 214, the needle head 216, and consequently, the needles 112, 132, move up or down to the desired vertical position. A belt driven rotating potentiometer is coupled to the screw shaft 214 to provide vertical position feedback for the needle head 216. Power to the drive motor 212 and the feedback from the potentiometer are interfaced to the control system 160 to allow accurate positioning of the needles 112, 132. Those skilled in the art will recognize that other mechanisms may be used for the linear actuator mechanism without interfering with the objects and advantages of the present invention.

Figure 4:
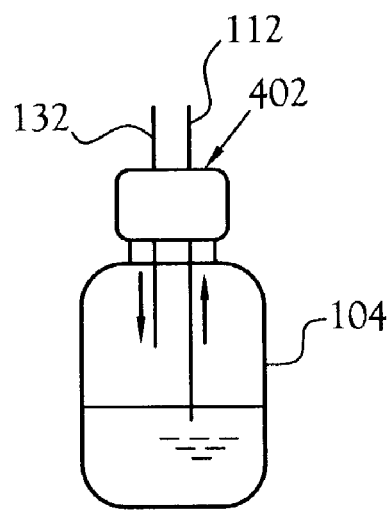
FIG. 4 illustrates a dual, parallel needle assembly used for liquid transfer.
Figure 5:
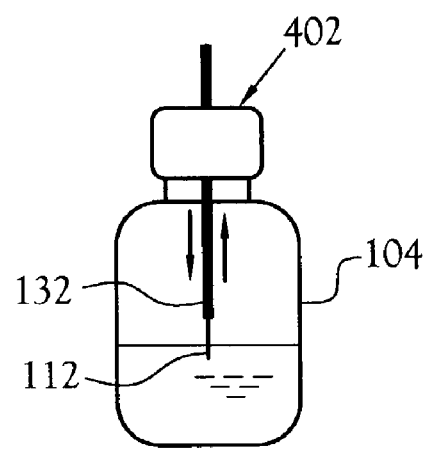
FIG. 5 illustrates a concentric needle assembly used for liquid transfer.
Figure 6:
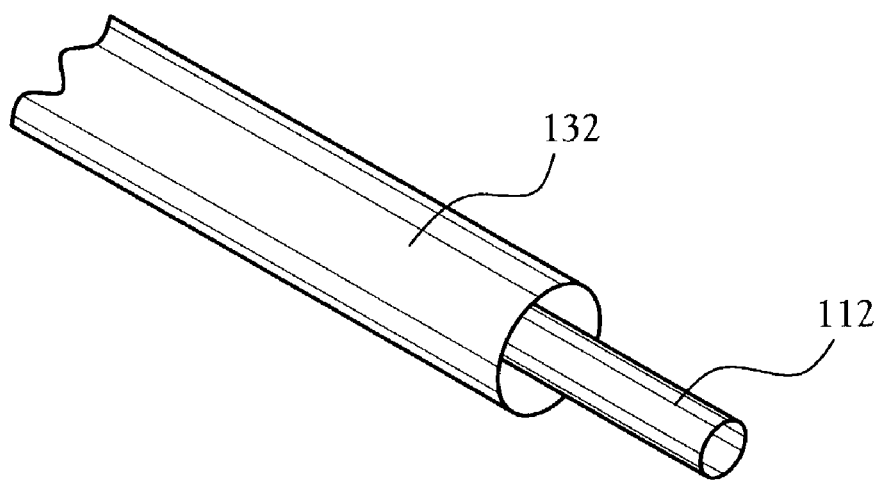
FIG. 6 illustrates a close-up view of the concentric needle assembly used for liquid transfer.

The needles 112, 132 provide a gas inlet to the septum-sealed reagent vials 104 and a liquid outlet from the vials 104. In the preferred embodiment, the needles 112, 132 are comprised of separate, concentric needles. In this embodiment, which is shown in FIGS. 5 and 6, gas enters the vial 104 through the annulus between the inner needle 112 and the outer needle 132, and the increasing gas pressure in the vial 104 forces liquid through the inner needle 112. The gas needle 132 is positioned higher than the liquid needle 112, thereby avoiding the formation of bubbles near the inlet of the liquid needle 112. In an alternative embodiment, shown in FIG. 4, separate, parallel needles are used for the gas inlet 132 and liquid outlet 112.

Both needle embodiments deliver liquids with the required accuracy and reproducibility, but the concentric needle embodiment offers several advantages over the parallel needle embodiment. First, the concentric design allows for the use of a smaller gauge needle 112 for liquid delivery. This reduces the effect of sudden pressure changes and thus provides more control during the liquid delivery. Second, the increased structural integrity provided by the larger gas needle 132 dramatically reduces the possibility of bending the liquid needle 112, even when the liquid needle 112 has a blunt tip (a blunt tip affords more accurate liquid deliveries than a slanted needle tip). The added strength eliminates the need for a needle guide or other means to prevent the bending of small gauge needles. Finally, a common problem encountered in repeated punctures of a septum 402 with a needle is "coring," or the shredding of small pieces of the septum material with the needle annulus. The resulted pieces lodge in the needle and block the flow of gas or liquid. This problem especially holds for larger gauge needles. Since the smaller gauge needle forms a "pilot" hole for the larger gauge needle, the concentric needle design greatly reduces the incidence of septum coring. Thus, the concentric design simultaneously allows the use of a non-bending, small gauge liquid needle 112 (to better control liquid delivery) and a non-coring, large gauge gas needle 132 (to provide structural integrity). A more detailed discussion of the needle configuration is disclosed in a related patent application Ser. No. 09/795,214 filed on Feb. 28, 2001 by Zigler, et al.

The gas (for example, nitrogen, helium, argon, or other non-reactive gas) used to pressurize the reagent vials 104 is delivered to the needles 132 through electronic mass flow controllers 134. The mass flow controllers 134 are commercially available devices that are interfaced to the control system 160 to allow remote gas flow set points and feedback. The mass flow controllers 134 control the gas flow to within less than 1 standard cm3/minute.

The liquid outlet needle 112 is connected to small-bore flexible tubing (for example, 1/16" outside diameter Teflon or polyethylene tubing) to route the liquid during the transfer process. To ensure the successful transfer of liquid, the reagent delivery system 10 employs liquid sensors 116 that detect the presence of liquid in the tubing and supply this data to the control system 160. The preferred embodiment uses a miniature ultrasonic transmitter and receiver affixed to the outside of the tubing, such as the commercially-available detectors manufactured by Introtek. When liquid is present in the tubing, the receiver generates a signal that is sent to the control system 160.

The liquid sensor 116 allows an operator to fill the reagent vials 104 in the rotary carousel 102 with any volume of liquid, and then perform an "auto-detect" sequence to determine the quantity of liquid in the vials. Thus, a key feature of the reagent delivery system 10 is that the operator does not have to measure the volume of liquid, thereby facilitating the set up process. An important feature of the liquid sensors 116 is that they do not directly contact the liquid, which eliminates the possibility of reagent contamination and detector corrosion.

FIG. 1 also shows the FDG production system 120, which includes the equipment and processes necessary to produce FDG. This equipment includes an accelerator, a target chamber, and a reaction vessel. The preferred embodiment uses the reaction vessel disclosed in the above-referenced patent application Ser. No. 09/569,780, filed on May 12, 2000, which contains a more detailed discussion of the equipment and the process.

Electronically controlled valves are used in the reagent delivery system 10 to route the flow of reagents and solvents throughout the automated apparatus for multi-batch production of FDG. Critical valves provide positional feedback to the control system 160 to ensure proper operation. The materials of construction for all the valves, tubing, and fittings are selected to minimize cross-contamination and dead space. These components are commercially available, for example, the valves are readily available through the Hamilton Company.

Figure 3:
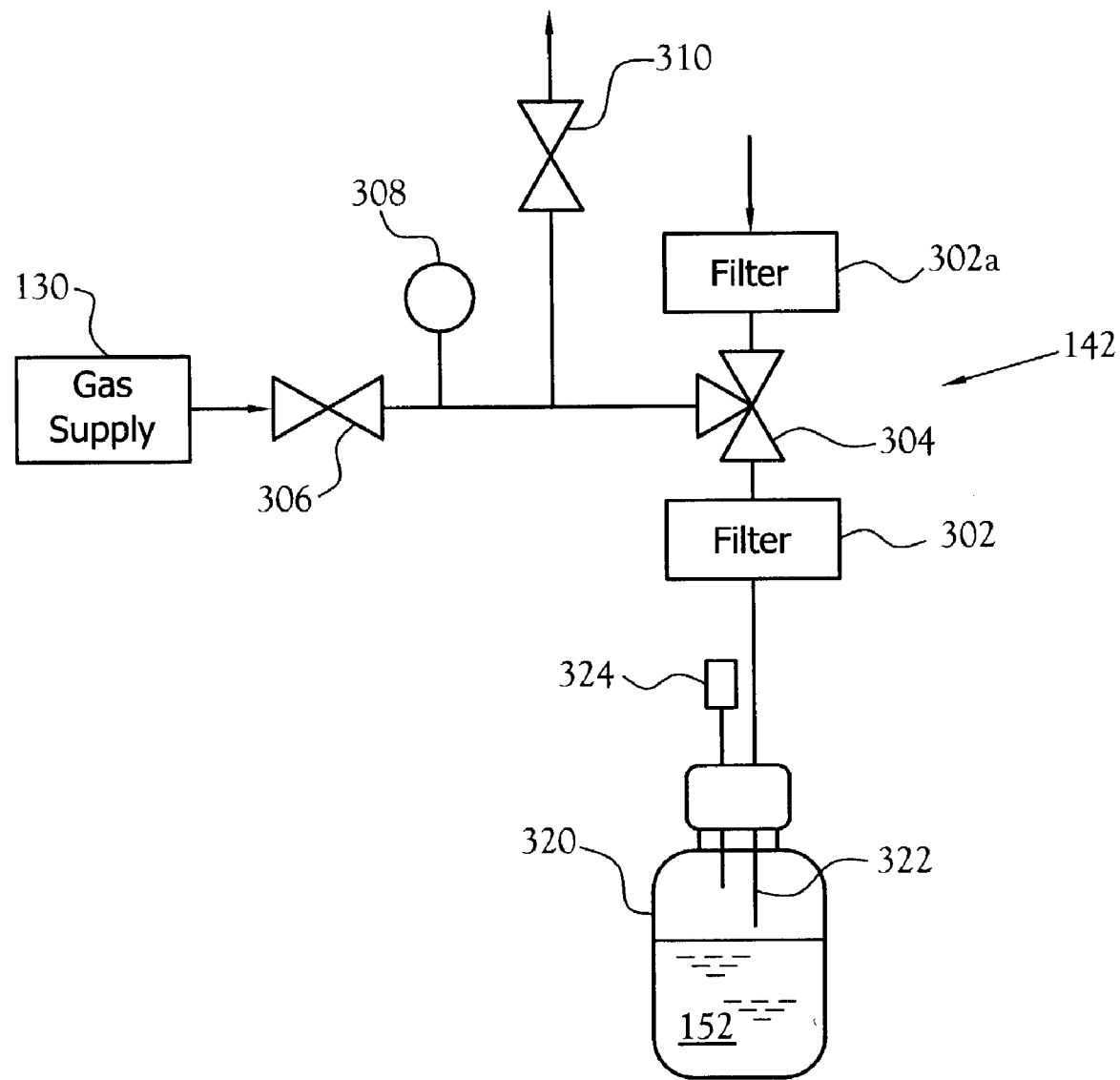
FIG. 3 is a block diagram of the automated pressure integrity test for the membrane filtration device.

FIGS. 1 and 3 show the filter assembly 142, which includes an automated pressure integrity test. The membrane filters 302 are commercially available devices designed for the removal of bacterial organisms from the product before it enters the final product vial 320. In order to ensure complete removal of bacteria, it is necessary to maintain the integrity of the membrane filters 302 during the filtration process. Operators assure this by testing the integrity of the wetted membrane filters 302 after completing the filtration process. The two most commonly used integrity tests are the bubble point test and the pressure retention test. In the bubble point test, the wetted membrane filtration device is attached to a source of compressed gas and the pressure slowly increased until gas passes through the membrane (i.e., the outlet of the membrane filtration device "bubbles" when placed in water). In the pressure retention test, the pressure of the gas on the wetted membrane is set to a point just below the bubble point. After initial pressurization, the supply of gas is removed, and the pressure is monitored to determine if the membrane "holds" pressure. Both integrity test methods typically involve manual manipulation of the membrane filtration device and, since the membranes contain residual FDG, result in radiation exposure to the operator.

In the illustrated embodiment, an automatic pressure integrity test, based on the pressure retention method, reduces manual manipulation of the filter assembly 142, thereby reducing radiation exposure to the operator. Referring to FIG. 3, the automated pressure integrity test components include a supply valve 306, which isolates the nitrogen gas supply from the filter assembly 142, a pressure sensor 308, a 3-way stopcock or isolation valve 304 which isolates the membrane filters 302 from the pressure sensor 308, and a vent valve 310 for exhausting the pressure after the test is completed. Referring to the flow chart in FIG. 9, the control system 160 opens the supply valve 306 and positions the isolation valve 304 such that one of the membrane filters 302 is pressurized with nitrogen or another gas. After the membrane filter 302 is pressurized, the control system 160 closes supply valve 306, and the control system 160 monitors the pressure sensor 308. After the testing period is completed, the pressure is vented by the control system 160 opening vent valve 310, which exhausts into a waste collector. This test is repeated for the other membrane filter 302. If both of the membrane filters 302 have no pressure loss over the time period tested, then the previous batch of FDG is deemed to have been properly filtered. Those skilled in the art will recognize that other plumbing arrangements for pressurizing and monitoring the filter assembly 142 may be used without interfering with the objects and advantages of the present invention. Another embodiment of the filter assembly 142 uses manual control of the filter assembly 142. In the manual control embodiment, the operator monitors the pressure at the pressure sensor 308 and manually operates the valves as described above.

In the preferred embodiment, the control system 160 includes a personal computer communicating with a microcontroller which interfaces with the various components of the reagent delivery system 10. The personal computer is running automation software by Intellution, Inc. Those skilled in the art will recognize that other means for controlling the reagent delivery system may be used without interfering with the objects and advantages of the present invention. For example, a dedicated controller with appropriate software may be used instead of the personal computer and microcontroller.

Figure 7:
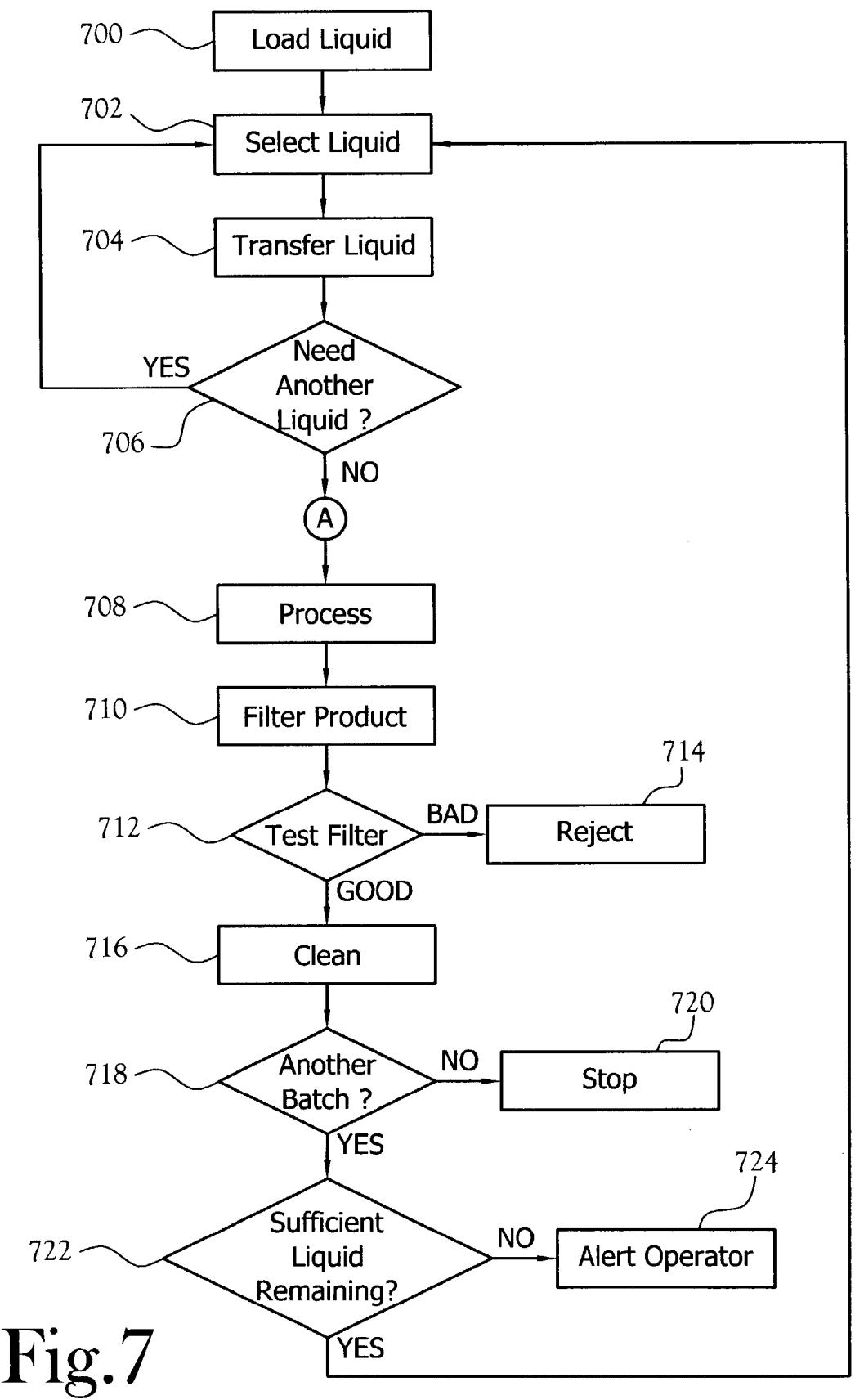
FIG. 7 is a flow chart of the process for multi-batch production of FDG.
Figure 8:
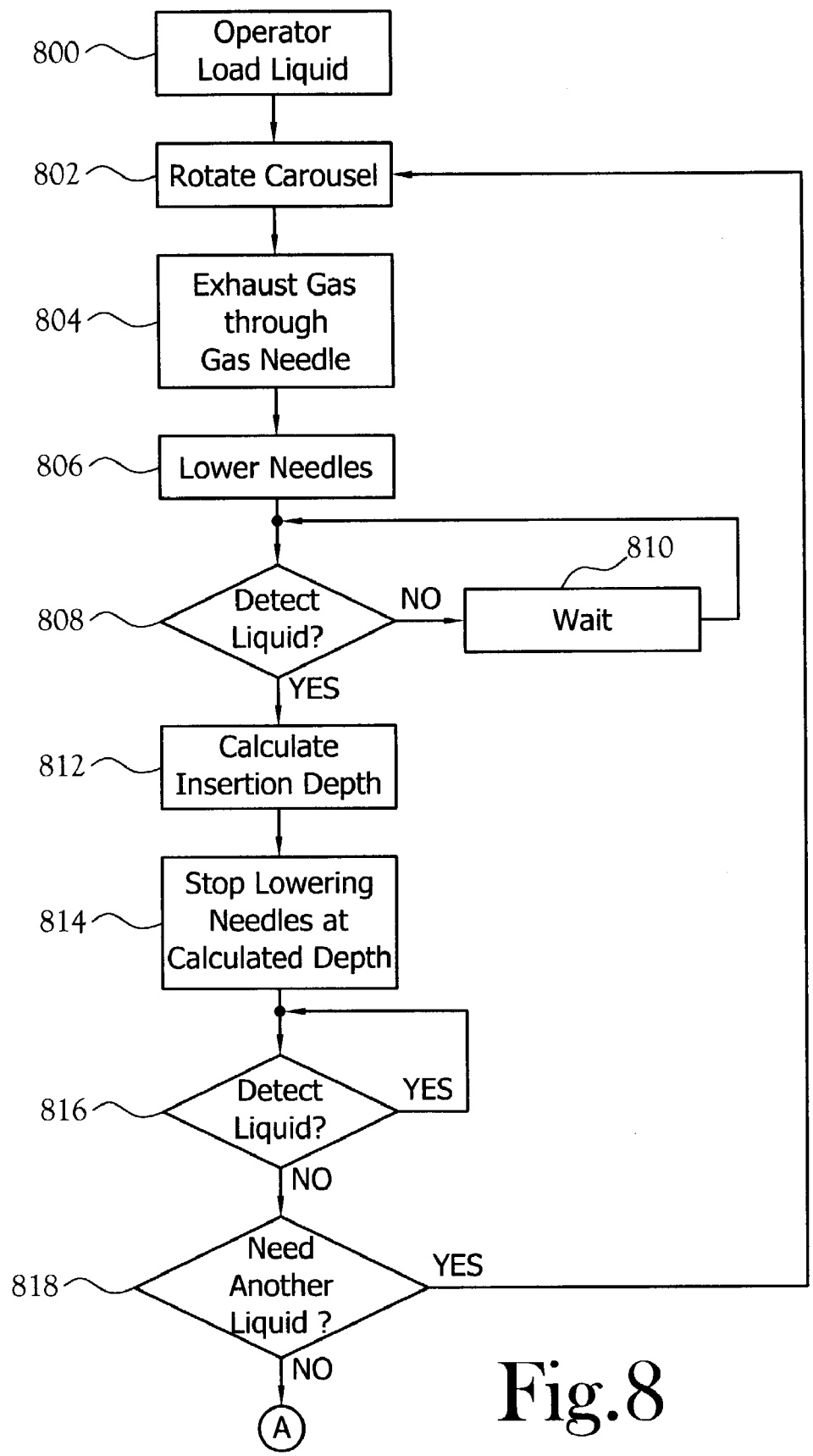
FIG. 8 is a flow chart of the process for the delivery of reagents and solvents to the FDG production system.

Referring to FIGS. 7 and 8 for the operation of the invention, the operator places 700 vials 104 containing the proper quantities of reagents and solvents in the rotating carousel 102. The operator then remotely operates the reagent delivery system 10 in order to produce multiple batches of FDG. The control system 160 determines which vials 104 the reagent delivery system 10 needs for its current operation 702, for example, target exposure, FDG production, or cleaning, and the control system 160 causes the rotating carousel 102 to rotate so that the appropriate vials 104 are positioned under the needles 112, 132. The control system 160 also aligns the various valves and mass flow controllers. The control system 160 then lowers 806 the needles 112, 132, penetrating the septum seal of the vials 104. After penetration, a controlled flow of gas exits needle 132 and the liquid sensors 116 monitor whether the needle 112 has reached the liquid surface in the vial 104, as indicated by detecting liquid in the tubing 808. The control system 160 determines the position of the linear actuator 114 corresponding to the liquid level in the vial 104. The control system 160 causes the linear actuator 114 to descend into the liquid in the vial 104 to a depth corresponding to the liquid volume required for the current operation 812, 814. Once that volume of liquid has been pushed through the needle 112, the liquid level falls below the opening of the needle 112, ensuring that only the predetermined volume of liquid has entered the reagent delivery system 10. The reagent delivery system 10 control system 160 then determines whether another reagent is necessary for the current operation 706, 818. If so, the control system 160 selects another vial 104 and repeats the above steps.

The reagent delivery system 10 uses a simple method to accurately and reproducibly dispense small quantities of reagents from the septum-sealed vials 104. The volume of reagent in the vial 104 may be calculated 812 from the diameter of the vial and the height of the liquid within the vial. For example, if the diameter of a vial 104 is 2 cm and the height of the liquid is 1 cm, then the volume of the liquid is ($\pi r2 \times h$), or 3.14 cm3. Different volumes may be dispensed from the vial 104 by changing the depth of the needle 112 used to remove the liquid.

With this method of liquid dispensing, only two sources of error contribute to variation in the volume of delivered reagent: error in the diameter of the vial 104 and error in the vertical position of the needle 112. The design of the reagent delivery system 10 minimizes the first source of error by specifying commercially-available vials with tight internal diameter tolerances, such as those sold by Kimble Glass Inc. The second source of error is minimized by accurately controlling the needle position with a linear actuator 114.

Figure 9:
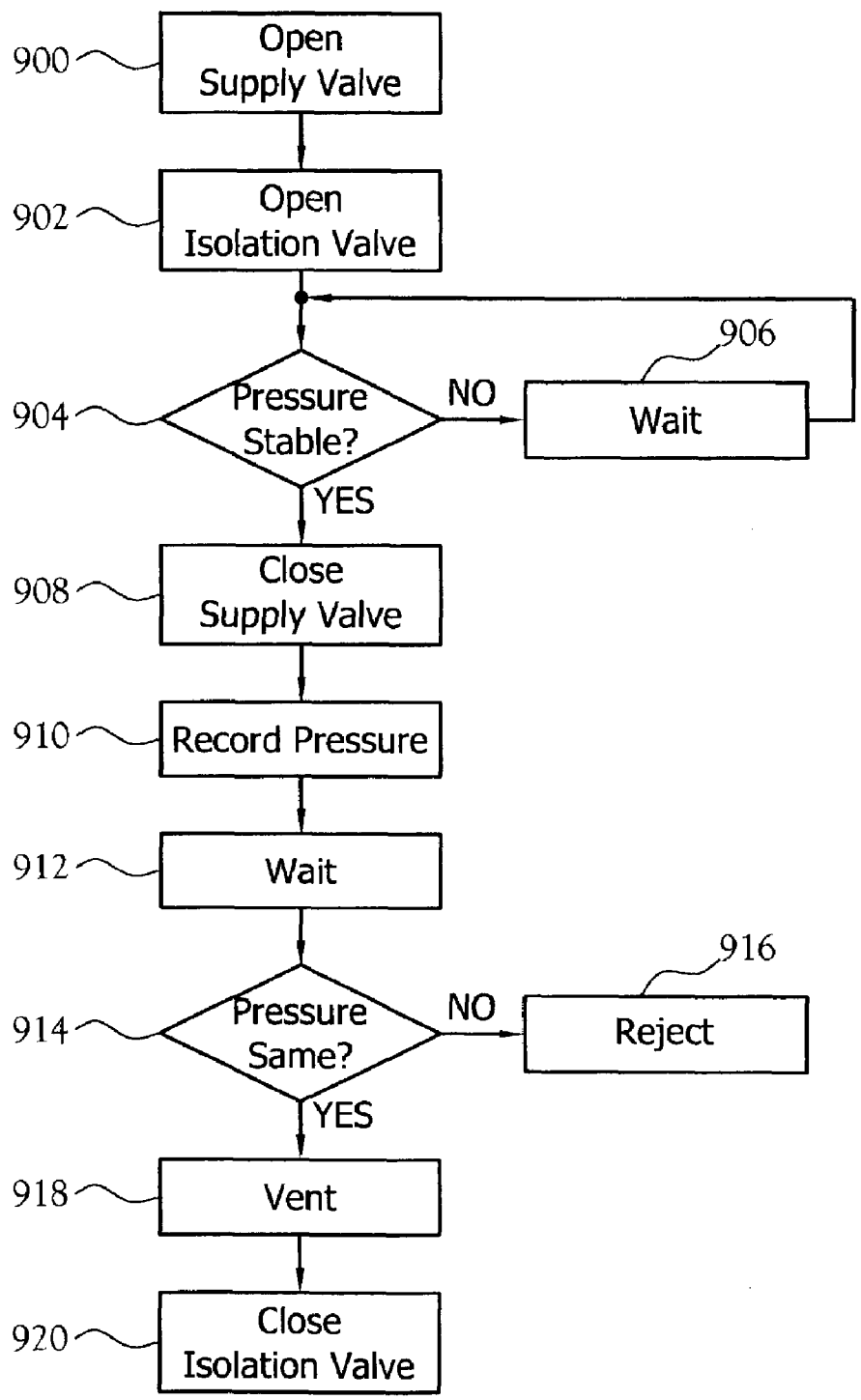
FIG. 9 is a flow chart of the process for the automatic pressure integrity test of the filter assembly.

After the processing equipment 120 has produced a batch of FDG 708, the reagent delivery system 10 uses gas pressure to push the product 710 through the filter assembly 142 and into the final product vial 320. The next step 712 is to verify the integrity of the filter assembly 142. Referring to FIG. 9, after the product leaves the filter assembly 142, the gas supply valve 306 is opened 900 and the isolation valve 304 is opened 902. After one or both membrane filters are pressurized, the gas supply valve 306 is closed 908. The pressure is then monitored 914 with pressure sensor 308, and if the pressure falls, the final product 152 is rejected 916 and must be refiltered. If the pressure remains substantially the same 914, the final product 152 is considered properly filtered. After the final pressure measurement, the vent valve 310 is opened 918, the pressure is vented to a waste system, the vent valve 310 is closed, and the isolation valve 304 is closed 920. The reagent delivery system 10 is then cleaned 716 by extracting the necessary solvents from the vials 104 and routing the solvents through the reagent delivery system 10.

Referring to FIG. 7, the control system 160 then determines whether a sufficient volume of reagents and solvents remain on the rotary carousel 102 for another batch of FDG to be produced 722. If so, the process repeats until the desired number of batches have been produced. If not, the control system 160 alerts the operator.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, we claim:

1. A method for producing multiple batches of a radiopharmaceutical, said method comprising:
   (a) manually providing at least one reagent to an apparatus for automatically producing a plurality of batches of the radiopharmaceutical, said apparatus having an accelerator, a target chamber, and a reaction vessel;
   (b) transferring said at least one reagent to said apparatus;
   (c) processing said at least one reagent wherein said radiopharmaceutical is produced, said step of processing includes the steps of:
   transferring said at least one reagent to the accelerator;
   transferring said at least one reagent to said target chamber; and
   transferring said at least one reagent to said reaction vessel;
   (d) filtering said radiopharmaceutical;
   (e) delivering said radiopharmaceutical to a container;
   (f) cleaning said apparatus, whereby said apparatus is in a condition for preparing another batch of the radiopharmaceutical; and
   (g) repeating the transferring, the processing, the filtering, the delivering, and the cleaning to produce a selected number of said plurality of batches of said radiopharmaceutical.

2. The method of claim 1 further comprising initiating production after said manually providing said at least one reagent,
   wherein said transferring, said processing, and said delivering are performed automatically and sequentially upon said initiation.

3. The method of claim 2 wherein said cleaning is performed automatically after said delivering.

4. The method of claim 1 wherein said cleaning comprises:
   transferring a solvent to said apparatus;
   automatically routing said solvent through said apparatus; and
   exhausting said solvent from said apparatus.

5. The method of claim 1 wherein the radiopharmaceutical includes fluorine-18.

6. The method of claim 1 further comprising pressure integrity testing of a filter assembly after said cleaning of said apparatus.

7. The method of claim 6 wherein said pressure integrity testing comprises:
   pressurizing a downstream side of a first filter with a gas supply at a specified pressure;
   isolating said gas supply from said first filter;
   monitoring a first filter gas pressure on said downstream side of said first filter for a specified time;
   venting said first filter gas pressure;
   rejecting said first filter if monitored said first filter gas pressure is not substantially equal to said specified pressure;
   pressurizing an upstream side of a second filter with said gas supply at said specified pressure, said second filter downstream of said first filter;
   isolating said gas supply from said second filter;
   monitoring a second filter gas pressure on said upstream side of said second filter for a specified time;
   venting said second filter gas pressure; and
   rejecting said second filter if monitored said second filter gas pressure is not substantially equal to said specified pressure.

8. A method for producing multiple batches of a fluorine-18 radiopharmaceutical, said method comprising:
   (a) manually providing at least one reagent that is capable of undergoing a nucleophilic substitution reaction to form the fluorine-18 radiopharmaceutical, to an apparatus for automatically producing a plurality of batches of the fluorine-18 radiopharmaceutical, said apparatus having a fluorine-18 fluoride ion generating accelerator, a target chamber, a reaction vessel, and a filter assembly;

(b) automatically transferring said at least one reagent to said apparatus;

(c) automatically processing said at least one reagent through said fluorine-18 fluoride ion generating accelerator, said target chamber, and said reaction vessel wherein a fluorine-18 radiopharmaceutical is produced;

(d) filtering said fluorine-18 radiopharmaceutical;

(e) delivering said fluorine-18 radiopharmaceutical to a container;

(f) cleaning said apparatus, whereby said apparatus is in a condition for preparing another batch of said fluorine-18 radiopharmaceutical; and (g) repeating manually providing, automatically transferring, automatically processing, filtering, delivering, and cleaning.

9. The method of claim 8 wherein said filtering is performed automatically after said automatically processing.

10. The method of claim 8 wherein said delivering is performed automatically after said filtering.

11. The method of claim 8 wherein said cleaning is performed automatically after said delivering.

12. The method of claim 8 further comprising performing pressure integrity testing automatically after said cleaning.

13. The method of claim 8 wherein said filtering, said delivering, and said cleaning are performed automatically and sequentially after said automatically processing.

14. The method of claim 8 wherein said filtering, said delivering, said cleaning, and said testing are performed automatically and sequentially after said automatically processing.

* * * * *